United States Patent [19]

Agreda et al.

[11] Patent Number: 5,026,931

[45] Date of Patent: Jun. 25, 1991

[54] PROCESS FOR PREPARING A PRODUCT STREAM RICH IN NAPHTHALENE AND 2-MONOIODONAPHTHALENE

[75] Inventors: Victor H. Agreda; Thomas H. Larkins, Jr., both of Kingsport, Tenn.

[73] Assignee: Eastman Kodak Company, Rochester, N.Y.

[21] Appl. No.: 580,418

[22] Filed: Sep. 10, 1990

[51] Int. Cl.$^5$ ............................................... C07C 17/34
[52] U.S. Cl. ..................................... 570/204; 570/190
[58] Field of Search ................................ 570/204, 190

[56] References Cited

U.S. PATENT DOCUMENTS

| | | | |
|---|---|---|---|
| 2,866,828 | 12/1958 | Crowder | 570/204 |
| 4,746,758 | 5/1988 | Rule et al. | 570/204 |
| 4,749,817 | 6/1988 | George et al. | 570/204 |
| 4,792,642 | 12/1988 | Rule et al. | 570/204 |
| 4,808,759 | 2/1989 | Paparatto | 570/204 |
| 4,822,929 | 4/1989 | Paparatto | 570/204 |
| 4,827,057 | 5/1989 | Kasbaver et al. | 570/204 |

FOREIGN PATENT DOCUMENTS 24776 10/1965 Japan .................................. 570/204

*Primary Examiner*—Werren B. Lone
*Attorney, Agent, or Firm*—Charles R. Martin; William P. Heath, Jr.

[57] ABSTRACT

Disclosed is a process comprising preparing a product stream rich in naphthalene and 2-monoiodonaphthalene comprising contacting hydrogen and a feed stream containing iodonaphthalenes selected from the group consisting of monoiodonaphthalene, diiodonaphthalene and triiodonaphthalene and mixtures thereof with an X or Y type zeolite containing an ion selected from the group consisting of sodium, potassium and rubidium and a metal selected from the group selected from the group consisting of palladium, platinum, rhodium and ruthenium.

6 Claims, No Drawings

PROCESS FOR PREPARING A PRODUCT STREAM RICH IN NAPHTHALENE AND 2-MONOIODONAPHTHALENE

This invention relates to a process for preparation of a product stream rich in naphthalene and 2-monoiodonaphthalene.

The compound 2,6-dimethyl naphthalene dicarboxylate is a particularly desirable material for use in the manufacture of polyesters which have excellent barrier properties in packaging applications.

This compound can be prepared using a number of different methods, including the carboxylation of 2,6-diiodonaphthalene. The compound 2,6-diiodonaphthalene in turn can be prepared in a variety of ways, including reacting naphthalene with oxygen and iodine in the presence of a zeolite catalyst in accordance with U.S. Pat. No. 4,746,758.

Although this oxyiodination method for preparation of 2,6-diiodonaphthalene has many desirable features, the yield of 2,6-diiodonaphthalene is fairly low. Along with the desired 2,6-diiodonaphthalene many other unwanted iodonaphthalene compounds are also produced, such as 1.monoiodonaphthalene, 2,7-diiodonaphthalene, 2,5-diidonaphthalene, triiodonaphthalenes and tetraiodonaphthalenes. Due to cost and other considerations, these unwanted iodonaphthalenes must be recycled to the oxyiodination reaction.

Research has shown that the oxyiodination reaction described in U.S. Pat. No. 4,746,758 has a selective aspect to it in that the amount of 2,6-diiodonaphthalene which is produced depends in large measure on the materials fed to the oxyiodination reaction. For example, oxyiodination of naphthalene and 2-momoiodonaphthalene tends to form the desired 2,6-diiodonaphthalene more so than oxyiodination of other iodonaphthaienes such as 1-monoiodonaphthalene, which leads to the formation of undesired iodonaphthalenes. Thus, the greater the amount of 2-momoiodonaphthalene and naphthalene which is contained in the stream recycled to the oxyiodination reaction the greater the amount of 2,6diiodonaphthalene that will be produced in the oxyiodination reaction.

U.S. Pat. No. 4,749,817 describes the selective hydrodechlorination of polychlorobenzenes to monochlorobenzene and dichlorobenzenes in the presence of a sulfide platinum or palladium catalyst.

In summary, this process can be thought of as a process wherein the mixed iodonaphthalene stream which remains after the 2,6-diiodonaphthalene is removed from the product stream of the oxyiodination reaction disclosed in U.S. Pat. No. 4,746,758 is contacted with hydrogen over a zeolite catalyst. As a result, the balance of mixed iodonaphthalenes is shifted so as to substantially increase the amount of 2-monoiodonaphthalene and naphthalene.

Broadly this process can be defined as a process for preparing a product stream rich in naphthalene and 2-monoiodonaphthalene comprising contacting, at a temperature in the range of 125 to 350° C, hydrogen and a feed stream containing iodonaphthalenes selected from the group consisting of monoiodonaphthalene, diiodonaphthalene and triiodonaphthalene and mixtures thereof with an X or Y type zeolite containing an ion selected from the group consisting of sodium, potassium and rubidium and a metal selected from the group selected from the group consisting of palladium, platinum, rhodium and ruthenium.

As described earlier, the feed stream for the process of this invention is the product stream of the oxyiodination reaction after most of the 2,6-diiodonaphthalene has been removed. The composition of the feed stream can therefor vary widely depending on the products made in the oxyiodination reaction. Typically, the feed stream can range from 100% 1-monoiodonaphthalene to any combination of mono, di, and tri iodinated naphthalenes. In one preferred embodiment, the feed stream is a mixture of monoiodonaphthalenes consisting of approximately 50% 1-monoiodonaphthalene, and 50% diiodonaphthalene. In another preferred embodiment the feed stream is a mixture of di, tri, and tetraiodonaphthalenes consisting approximately of 50% beta substituted diiodonaphthalenes (eg. 2,7-diiodonaphthalene), 40% alpha or alpha-beta substituted diiodonaphthalenes (eg. 1,5-diiodonaphthalene, 1,7-diiodonaphthalene), 8% triiodonaphthalenes, and 2% tetraiodonaphthalenes.

The net result of the reaction occurring in the presence of the zeolite catalyst is the replacement of iodine with hydrogen at all the alpha positions and all but one of the beta positions. Naphthalene, iodine, and hydrogen iodide are also produced as a result of such reactions.

The feed ratio of hydrogen to iodonaphthalenes depends on the feed composition and the desired conversion. For example, more highly iodinated feeds or higher desired conversions require higher hydrogen feed rates. Of course, iodonaphthalenes not converted to 2-monoiodonaphthalene and naphthalene in one pass through the reactor can be fractionated and recycled until the only products are 2.monoiodonaphthalene, naphthalene, iodine, and hydrogen iodide.

In this invention the term "hydrogen" has a broader meaning than merely the compound $H_2$ and includes any source of hydrogen atoms that will permit the practice of the invention. Elemental hydrogen is the preferred source.

The process of this invention can be carried out in a packed bed reactor with downward or upward flow of reactants. Dimensions and geometry of the reactor can be tailored to the desired conversions for different feed compositions, following standard design practices.

In a preferred embodiment the process can be operated continuously by the continuous addition of the feed stream and optionally, naphthalene, if desired or necessary for use as a solvent for highly iodinated iodonaphthalenes. However, the process can also be carried out on a batch or semi batch system as desired.

The space velocity may be readily selected by the artisan depending on the feed composition, catalyst used, and the desired conversion and product distribution.

The pressure at which these reactions are carried out is not critical and ranges from about subatmospheric to about 1500 psig. The optimal pressure varies depending on the catalyst used but should preferably be in the range of atmospheric to 500 psig.

The temperature at which the reactions are carried out ranges from about 175 degrees C to about 350 degrees C. A preferred temperature range, so as to avoid freezing of some reaction mixtures or thermal decomposition of others, is between about 200 and 300 degrees C. Depending on the feed composition, the iodonaphthalenes may be in the vapor phase, liquid phase, or both. A more preferred temperature range to be used is between 215 and 250 degrees C. The optimal temperature depends on the catalyst and the composition of the feed material to be reacted.

The zeolites useful in this invention are the type X or type Y which contain one or more alkali metal ions which can be sodium, potassium, or rubidium, and one or more noble metals which can be ruthenium, rhodium, palladium, or platinum. A preferred catalyst is zeolite type 13X. In its most preferred embodiment the catalyst is a 13X zeolite containing potassium as the alkali metal ion and palladium or ruthenium as the noble metal. Most preferably 100% of the cations are replaced with the alkali metal ions so that no hydrogen ion sites are left. The exact weight % concentration at 100% exchange depends on the zeolite and the counterion. For example, 100% exchange with potassium on 13X zeolite corresponds to 18 weight % potassium. The desired noble metal % concentration ranges from 0.001 weight % to 1.0 weight The preferred concentration is about 0.01 weight %. The different catalysts provide different reaction rates and selectivity, with the most preferred catalysts providing the highest selectivity to the desired 2-monoiodonaphthalene. The zeolites as well as the method of preparing the zeolites so that they contain an alkali metal ion and a noble metal are well known in the art.

The product stream resulting from practice of this invention is rich in naphthalene and 2-monoiodonaphthalene. The amount of 2-monoiodonaphthalene produced depends on such factors as the composition of the feed, catalyst, design of the reactor, and temperature and pressure at which the reactor is operated. In a preferred embodiment the process would be practiced so that an optimum is achieved between selective hydrodehalogenation (at 100% hydrodehalogenation, naphthalene would be the only product) and incomplete hydrodehalogenation that would maximize the amount of 2-monoiodonaphthalene in the product but that might require that unreacted, or partially hydrodehalogenated iodonaphthalenes be separated from the product and recycled for further selective hydrodehalogenation.

The following examples are presented to illustrate the present invention but are not intended to limit in anyway the scope of the invention which is defined by the appended claims.

EXAMPLE 1

A catalyst suitable for use in the process of this invention is prepared. A solution was prepared containing 0.1 g palladium chloride, 6 ml concentrated hydrochloric acid, and 800 ml water. This solution was heated to 60° C and 200 ml potassium-exchanged 13-X molecular sieve beads (20×40 mesh) were added rapidly with stirring. The resultant slurry was stirred gently for 15 minutes and the liquid was removed by decantation. The catalyst was washed by slurring four times in 500 ml water at 60° C. for 15 minutes each time and decanting the wash liquid. The catalyst was dried on a steam bath and then reduced in a hydrogen atmosphere at 300° C.

Using this catalyst, a mixture of 66 mole percent 2-monoiodonaphthalene and 34 mole percent 1-monoiodonaphthalene was continually passed at 10 g/hr over 50 ml of the catalyst at 275° C under a flow of 25 ml/minute hydrogen and 200 ml/minute nitrogen gas. At the end of four hours of the product stream was 61 mole percent naphthalene and 39 mole percent 2-monoiodonaphthalene. Free iodine and hydrogen iodide were detected in the product mixture.

EXAMPLE 2

A catalyst was prepared as in Example 1 except ruthenium chloride was used to introduce ruthenium as the noble metal instead of palladium.

A mixture of 77 mole percent 2-monoiodonaphthalene and 23 mole percent 1-monoiodonaphthalene was continuously passed at 10 g/hour over 50 ml of the catalyst at 250° C under a flow of 25 ml/minute hydrogen and 200 ml/minute nitrogen gas. At the end of three hours the product stream was 64 mole percent naphthalene, 35 mole percent 2-monoiodonaphthalene, and 1 mole percent 1-monoiodonaphthalene. Free iodine and hydrogen iodide were detected in the product stream.

Obviously, numerous modifications and variations of the present invention are possible in light of the above teachings. It is therefore to be understood that within the scope of the appended claims, the invention may be practiced otherwise than as specifically described herein.

We claim:

1. A process for preparing a product stream rich in naphthalene and 2-monoiodonaphthalene and low in 1-diiodonaphthalene comprising contacting, at a temperature in the range of 125 to 350° C, hydrogen and a feed stream containing iodonaphthalenes selected from the group consisting of monoiodonaphthalene, diiodonaphthalene and triiodonaphthalene and mixtures thereof with an X or Y type zeolite containing an ion selected from the group consisting of sodium, potassium and rubidium and a metal selected from the group selected from the group consisting of palladium, platinum, rhodium and ruthenium.

2. The process of claim 1 wherein the amount of metal is in the range of 0.001 to 1.0 weight percent.

3. The process of claim 2 wherein the amount of metal is in the range of 0.001 to 0.1 weight percent.

4. The process of claim 1 wherein the zeolite is the 13X type, the ion is potassium and the metal is selected from the group consisting of rhodium and ruthenium.

5. The process of claim 1 wherein naphthalene is additionally contacted with the zeolite.

6. The process of claim 1 wherein the temperature is in the range of 125° to 250° C.

* * * * *